(12) United States Patent
Pontisso et al.

(10) Patent No.: US 12,239,667 B2
(45) Date of Patent: Mar. 4, 2025

(54) EXTRACELLULAR VESICLES ISOLATED FROM GENETICALLY MODIFIED CELLS OVER-EXPRESSING SERPINB3 FOR USE IN MEDICINE

(71) Applicant: UNIVERSITA' DEGLI STUDI DI PADOVA, Padua (IT)

(72) Inventors: Patrizia Pontisso, Padua (IT); Maurizio Muraca, Padua (IT); Alessandra Biasiolo, Selvazzano Dentro (IT); Santina Quarta, Villaguattera di Rubano (IT); Mariagrazia Ruvoletto, Vigonovo (IT); Gianmarco Villano, Padua (IT)

(73) Assignee: UNIVERSITÀ DEGLI STUDI DI PADOVA, Padua (IT)

(*) Notice: Subject to any disclaimer, the term of this patent is extended or adjusted under 35 U.S.C. 154(b) by 721 days.

(21) Appl. No.: 17/430,739

(22) PCT Filed: Feb. 14, 2020

(86) PCT No.: PCT/IB2020/051244
§ 371 (c)(1),
(2) Date: Aug. 13, 2021

(87) PCT Pub. No.: WO2020/165851
PCT Pub. Date: Aug. 20, 2020

(65) Prior Publication Data
US 2022/0143098 A1 May 12, 2022

(30) Foreign Application Priority Data
Feb. 14, 2019 (IT) .................. 102019000002155

(51) Int. Cl.
*A61K 35/28* (2015.01)
*A01N 1/02* (2006.01)

(52) U.S. Cl.
CPC ............ *A61K 35/28* (2013.01); *A01N 1/0226* (2013.01)

(58) Field of Classification Search
None
See application file for complete search history.

(56) References Cited

U.S. PATENT DOCUMENTS

2018/0220642 A1   8/2018 March et al.
2020/0166524 A1*  5/2020 De Kleijn .......... G01N 33/6893

FOREIGN PATENT DOCUMENTS

WO   2014/013258 A1   1/2014

OTHER PUBLICATIONS

International Search Report and Written Opinion for corresponding Application No. PCT/IB2020/051244 (mailed Jun. 18, 2020).
Lai et al., "Proteolytic Potential of the MSC Exosome Proteome: Implications for an Exosome-Mediated Delivery of 2 Therapeutic Proteasome," Internat. J. Proteomics 91(7):2573-14 (2012).
Hall et al., "Delivery of Therapeutic Proteins via Extracellular Vesicles: Review and Potential Treatments for 3 Parkinson's Disease, Glioma, and Schwannoma," Cellular Mol. Neurobiol. 36(3):417-427 (2016).
Catanzaro et al., "SerpinB3/B4: Mediators of Ras-dDiven Inflammation and Oncogenesis," Cell Cycle 13(9):3155-3156 (2014).

* cited by examiner

*Primary Examiner* — Blaine Lankford
(74) *Attorney, Agent, or Firm* — Troutman Pepper Locke LLP

(57) ABSTRACT

The present invention concerns the therapeutic use of extracellular vesicles isolated from a genetically modified cell line over-expressing SerpinB3. In particular, said therapeutic use aimed at the treatment of acute pathologies characterized by ischemic or inflammatory tissue damage or by cell injury due to oxidative stress, such as cardiac, cerebral, intestinal, renal or limb ischaemia. Further examples of use consist of the preservation of transplant organs, including heart, lung, liver, bladder, pancreas and intestine. In a further aspect the invention relates to the use of a pharmaceutical composition comprising extracellular vesicles isolated from a genetically modified cell line over-expressing SerpinB3 and a pharmaceutically acceptable vehicle.

14 Claims, 4 Drawing Sheets

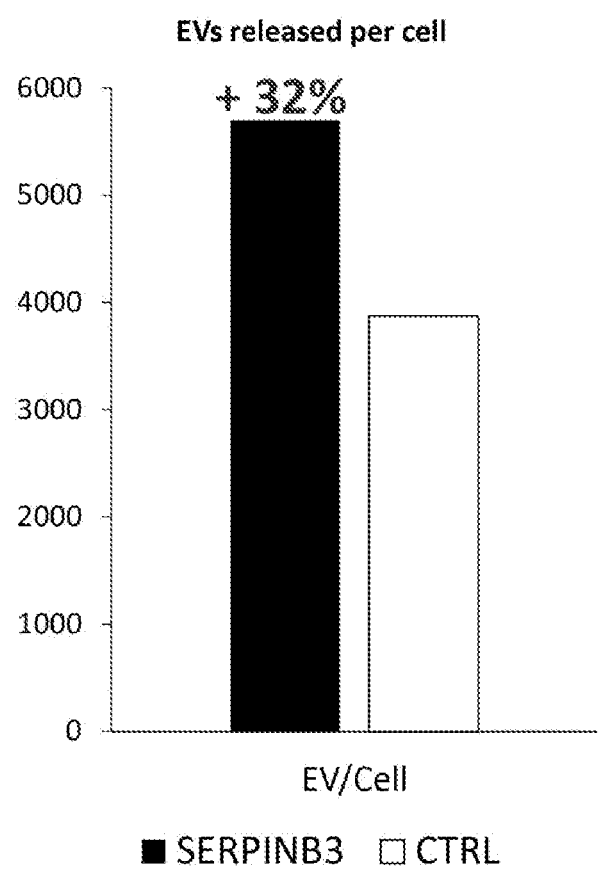

EXTRACELLULAR VESICLES ISOLATED FROM GENETICALLY MODIFIED CELLS OVER-EXPRESSING SERPINB3 FOR USE IN MEDICINE

This application is a national stage application under 35 U.S.C. § 371 of PCT Application No. PCT/IB2020/051244, filed Feb. 14, 2020, which claims the priority benefit of Italian Patent Application No. 102019000002155, filed Feb. 14, 2019, which are hereby incorporated by reference in their entirety.

The present invention concerns the therapeutic use of extracellular vesicles isolated from a genetically modified cell line over-expressing SerpinB3. In particular, said therapeutic use aimed at the treatment of acute pathologies characterized by ischemic or inflammatory tissue damage or by cell injury due to oxidative stress, such as cardiac, cerebral, intestinal, renal or limb ischaemia. Further examples of use consist of the preservation of transplant organs, including heart, lung, liver, bladder, pancreas and intestine.

In a further aspect the invention relates to the use of a pharmaceutical composition comprising extracellular vesicles isolated from a genetically modified cell line over-expressing SerpinB3 and a pharmaceutically acceptable vehicle.

STATE OF THE ART

The conditions that most frequently lead to suffering and cell death are ischemic situations, due to an inadequate blood supply to the tissues, or the excessive accumulation of toxic products that cause tissue oxidative stress. It has recently been documented that the SerpinB3 molecule is capable of counteracting cell death as it binds to mitochondrial components that activate the cascade of events leading to cell death (1). This molecule, present in the cells (2) in stem stage, is induced in organ cells that normally do not express it under conditions of reduced oxygen concentration (3) or excess of toxic compounds, such as iron (4). It is also able to induce cell proliferation by activating signal pathways involving beta-catenin (5) and Myc (6). The defence activity against cell death of SerpinB3 is carried out not only when the molecule is inside the cell, but also if the cells are put in contact with the molecule from the outside (3,5). Consequently, the possibility of counteracting suffering and tissue damage constitutes a therapeutic possibility. Examples of diseases that could benefit are those on an ischemic basis, such as cardiac, cerebral, intestinal, renal or limb ischaemia. Further examples of use consist of the preservation of transplant organs, including heart, lung, liver, bladder, pancreas and intestine. Additional conditions that could benefit are situations of tissue suffering such as in acute inflammation or due to toxic substances, such as alcohol and cigarette smoke.

The drugs developed to date to counteract ischemic and toxic cell injury act in a non-specific way by reducing the free radicals induced by oxidative stress. The limited efficacy often documented in this framework probably depends on the fact that the action exerted by the drug does not confer a greater resistance to cell death but limits itself to reducing the toxicity induced by the damage.

Interfering with the processes that regulate the blood supply to the tissues and preventing the supply of toxic products to the cells constitutes a therapeutic approach of significant clinical interest, but the drugs available so far have shown generally limited efficacy.

The extracellular vesicles (EV) are vesicles containing portions of cytoplasm surrounded by membrane, released by the cells into the microenvironment (7). They represent a heterogeneous population that comprises exosomes and micro-vesicles, in part distinguishable from each other based on size, composition and secretion modality.

EVs play an important role in intercellular communication: they can stimulate the target cells directly, through receptor-ligand interaction, or they can transfer ligands, receptors, proteins and nucleic acids (even mitochondria). The EVs are implicated in a variety of diseases and participate in tissue regeneration. The EVs therefore constitute a promising biological drug and can reproduce many of the therapeutic effects of cell therapies by eliminating or minimizing many of the problems related to the transplantation of living cells, such as the risk of tumour transformation, colonization of cells in sites other than those desired with unpredictable effect, immunological compatibility. Furthermore, the production of EVs is simpler than that of cells, with a significant reduction in costs. Some phase I clinical studies with EVs derived from dendritic cells for anti-tumour immunotherapy demonstrate that large-scale GMP production of these microparticles and their use at clinical level (8) is possible.

The aim of the present invention is therefore to provide a product for the treatment of pathologies affecting organs and tissues that are under suffering conditions of the ischemic type or oxidative stress, which has a good efficacy and which does not have the disadvantages found for drugs already known for the same therapy.

SUMMARY OF THE INVENTION

The present invention concerns the use as a medicament of extracellular vesicles isolated from a genetically modified cell line over-expressing SerpinB3. In particular, said therapeutic use is aimed at the treatment of pathologies characterized by ischemic cell injury or characterized by cell injury due to oxidative stress.

SerpinB3 molecule has recently been shown to be a protective agent against cell death under oxidative stress conditions. This molecule is naturally induced under stress conditions to increase cell survival and its proliferative capacity by activating specific signal pathways and the interaction with mitochondrial components that regulate the apoptotic cell death.

In a further aspect the invention relates to the use of a pharmaceutical composition comprising extracellular vesicles isolated from a cell line over-expressing SerpinB3 and a pharmaceutically acceptable vehicle.

In a further embodiment, the present invention relates to the use of extracellular vesicles isolated from a cell line over-expressing SerpinB3 for the preservation of organs for transplantation.

DESCRIPTION OF THE DRAWINGS

The invention will now be described in detail and with reference to the attached Figures in which:

FIG. 2 shows the quantification results of EVs released by cells. FIG. 2C shows the graph relating to the number of EVs released/cell in SerpinB3 over-expressing lines and in control lines, obtained as described in Example 3. SerpinB3 over-expressing cell lines are observed to release 32% more EVs than control lines.

DETAILED DESCRIPTION OF THE INVENTION

Figure 1:
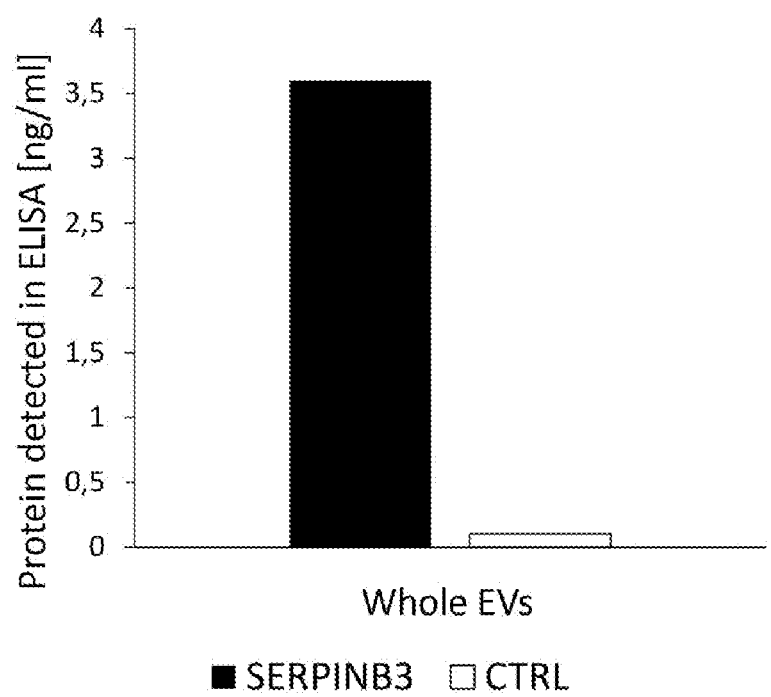
FIG. 1 shows the graph of the results in which the quantities of SerpinB3 protein detected by the ELISA assay were indicated. This measurement was carried out in whole EVs, both SerpinB3 over-expressing and control EVs, as explained in example 2.

The present invention concerns the use as a medicament of extracellular vesicles isolated from a genetically modified cell line over-expressing SerpinB3. In particular, said therapeutic use is applicable in the field of regenerative medicine and in particular in the treatment of pathologies characterized by ischemic cell injury or characterized by cell injury due to oxidative stress.

The pathologies characterized by ischemic cell injury are for example: myocardial, cerebral, intestinal, renal infarction, acute limb ischaemia.

The pathologies characterized by cell injury due to oxidative stress are for example: hypoxia of the donor organ in the context of heart, bladder, liver, lung, pancreas, intestine transplantation.

The EVs consist of portions of cytoplasm surrounded by membrane, released by cells into the microenvironment. The EVs of the present invention over-express SerpinB3 and protect tissues from cell death and participate in tissue regeneration and advantageously have the function of inducing specific phenotypes, immunomodulation and angiogenic activity.

In the present invention, "to over-express", "to hyper-express", "over-expressing" or "over-expression" when referring to SerpinB3, mean a genetically modified cell line that has a quantity of SerpinB3 markedly higher than that possibly present in the basal state of the cell.

The production of EVs is simpler than that of cells, with a significant reduction in costs (9).

The EVs are vesicles containing portions of cytoplasm surrounded by membrane, released by the cells into the microenvironment and are now considered the most important carriers of the biological signals responsible for intercellular communication. They can be easily isolated from cell cultures and have already been used as therapeutic tools. The EVs are complex biological particles that transmit a series of signals, and can therefore interfere at various levels with cell death processes, unlike the drugs currently in use, which act selectively on a specific metabolic pathway or stage.

The EVs have the advantage of being able to be isolated with fast and easy to perform techniques and can be conveniently produced and isolated in GMP certified laboratories for clinical use. The EVs are isolated from the cell culture medium by ultrafiltration, ultracentrifugation or column separation methods. The EVs can be stored at −80° C. or in liquid nitrogen, with or without cryopreservatives, for months without significant loss of biological activity.

In a preferred form, the invention concerns the use of extracellular vesicles isolated from a genetically modified cell line over-expressing SerpinB3, in the treatment of pathologies characterized by ischemic cell injury. This ischemic injury can be of the cardiac, cerebral, intestinal, renal or limb type. Further examples of use consist of the preservation of transplant organs, including heart, lung, liver, bladder, pancreas and intestine. Additional conditions that could benefit are situations of tissue suffering such as in acute inflammation or from toxic substances, such as alcohol and cigarette smoke.

Figure 3:
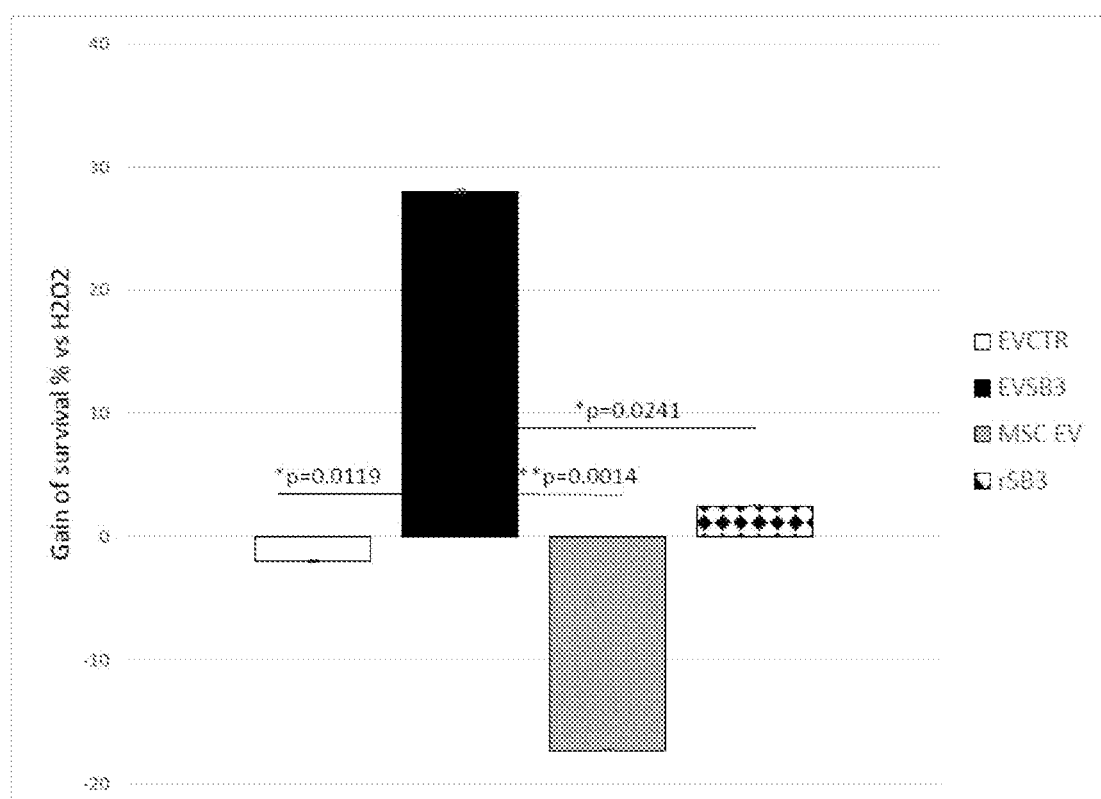
FIG. 3 shows the graph with the results of a cell mortality assay by MTT assay, in which the protection from oxidative damage by micro-vesicles over-expressing SerpinB3 (EV/SB3) occurs. Experimental design: treatment of HepG2 cells at 90% of semiconfluence with $H_2O_2$ 250 µMol or control medium in the presence or absence of different EV preparations. EVs deriving from HepG2 cells engineered to over-express SERPINB3=EV/SB3, EVs deriving from HepG2 cells transfected with the empty plasmid only=EV CTR, SerpinB3 recombinant protein at the same concentration present in the preparations of EV/SB3=rSB3 and EV deriving from MSC=MSC EV. All the EV preparations have been previously tested for SerpinB3 by ELISA and only the EV/SB3 preparation has tested positive, while the EV CTR and MSC EV preparations have not documented any detectable levels of SerpinB3.

As shown in FIG. 3 and Example 4, the extracellular vesicles over-expressing SerpinB3 show a surprising technical effect in protecting from oxidative damage in cells, which instead the non-overexpressing SerpinB3 extracellular vesicles (EVCTR and MSC EV) do not demonstrate.

Ischemic or toxic tissue damage can lead to irreversible tissue damage, leading up to the death of the individual in particularly serious situations. Interfering with these processes constitutes a therapeutic approach of significant clinical interest and the drugs available so far have shown generally limited efficacy. The EVs are complex biological particles that transmit a series of signals, resulting in a certain biological effect and can participate in cell regeneration. The present invention constitutes an innovative therapeutic approach because it proposes the use of EVs characterized by a high concentration of a molecule which confers resistance to cell death, amplifying the biological effects of these particles.

In an even more preferred form, the invention concerns the use of extracellular vesicles, in the treatment of pathologies characterized by cell injury due to oxidative stress, such as for example cardiac, cerebral, intestinal, renal or limb ischaemia. Further examples of use consist of the preservation of transplant organs, including heart, lung, liver, bladder, pancreas and intestine. Additional conditions that could benefit are situations of tissue suffering from toxic substances, such as alcohol and cigarette smoke.

The extracellular vesicles described in the present invention can be isolated from any cell line over-expressing SerpinB3. This cell line can be a genetically modified cell line to over-express SerpinB3, to obtain the production of extracellular vesicles with anti-apoptotic and pro-proliferative properties. Preferably, said cell line over-expressing SerpinB3 is derived from mesenchymal stromal cells.

In one embodiment, SerpinB3 is over-expressed on the membrane of said extracellular vesicles.

The EVs were generated from genetically modified cell lines to over-express SerpinB3, to obtain the production of EVs with anti-apoptotic and pro-proliferative properties. Based on the experimental data, the EVs described by the present invention can be used as regenerative therapy in diseases on ischemic base or due to oxidative stress.

In a further aspect the invention relates to the use of a pharmaceutical composition comprising extracellular vesicles isolated from a cell line over-expressing SerpinB3 and a pharmaceutically acceptable vehicle.

In one embodiment, the use of the composition comprising said extracellular vesicles is in the treatment of pathologies characterized by ischemic cell injury such as for example cardiac, cerebral, intestinal, renal or limb ischaemia.

In another aspect, the present invention relates to the use of extracellular vesicles isolated from a cell line over-expressing SerpinB3 for the preservation of organs for transplantation. In a preferred but not limiting embodiment, these organs are heart, lung, liver, bladder, pancreas and intestine.

In a further embodiment, the use of the composition comprising said extracellular vesicles is in the treatment of pathologies characterized by cell injury due to oxidative stress, such as in acute inflammation or due to toxic substances, such as alcohol and cigarette smoke.

The compositions according to the present invention can be in solid or liquid form. Such compositions can be for enteral and parenteral administration, intravenously, intraperitoneally, orally, sublingually, aerosol, inhalations, sprays, rectal, intraocular, topical or transdermal route.

The following examples of embodiments of the present invention are given below by way of illustration.

EXAMPLES

Example 1

EV Isolation Method: Ultrafiltration

Extracellular vesicles were obtained from genetically transfected lines to over-express SerpinB3 and from corresponding cells transfected with the empty control plasmid (5) only. The cells were obtained by stable transfection with Lipofetctamine 3000, using the plasmid vector pcDNA3.1 D/V5-His-Topo containing the resistance to the selection antibiotic G418 and the construct for SerpinB3 or with the plasmid as such for the control cell line. The transfected cells were then cloned and selected, using the antibiotic G418, added to the culture medium. At the end of this process SerpinB3 over-expressing clones and control clones were obtained. The best ones, in terms of protein expression, were used for the production of EVs.

The extracellular vesicles obtained from the cells that over-expressed SerpinB3 were in greater numbers and were positive for SerpinB3

1—Withdrawal of medium conditioned by over-expressing cells
2—Purification from cellular debris
3—Ultrafiltration (Amicon Filters, 100 kDa Cutoff)
4—The EVs thus obtained can be used immediately or stored in liquid nitrogen.

Example 2

Extracellular Vesicles (EV) Isolated from SERPINB3 Over-Expressing Cells Expose SERPINB3

An ELISA assay was carried out in order to verify the SerpinB3 expression on the EVs isolated from cells that over-express it.

SerpinB3 concentration was quantified by ELISA assay (HEPA Lisa, Xeptagen, Venice, Italy) following the manufacturer's instructions. Briefly, 100 µl of undiluted sample (whole EV, lysed EV, ultrafiltration eluate and Control medium) were incubated for 1 hour at room temperature on plates coated with rabbit anti-SerpinB3 capture antibody (10 µg/ml in PBS, pH 7.4) and previously blocked with a 10% solution of milk powder in PBS pH 7.4. Each sample was double tested and the concentration of SerpinB3 was determined by inserting a 6-point calibration curve obtained with scalar dilutions of a standard preparation of recombinant SerpinB3 in a range comprised between 16-0.25 ng/ml.

After washing, the presence of SerpinB3 was revealed by incubation with 100 µl of anti-SerpinB3 secondary antibody conjugated with streptavidin-horseradish peroxidase (0.5 µg/ml). The plate was developed with a ready-to-use TMB substrate solution. The colorimetric reaction was blocked by adding 1 ml/L of HCl (100 µl) and the optical density at 450 nm was measured using a Victor X3 (Perkin Elmer) plate multimedia reader. As can be seen from Table 1, only whole extracellular vesicles isolated from cells that have been genetically modified to over-express SerpinB3 are positive for this protein. The negativity for SerpinB3 in the lysates and in the conditioned medium suggests that this protein is associated with the outer envelope of EVs, rather than contained within it. Non-overexpressing SERPINB3 cells do not secrete EVs containing SERPINB3.

TABLE 1

| LOCALIZATION SERPINB3 | SERPINB3 EV | CONTROL EV |
|---|---|---|
| Conditioned medium | X | X |
| Whole EVs | ✓ | X |
| Ultrafiltration eluate | X | X |
| Lysed EVs | X | X |

These results are also visible from the graph of FIG. 1 in which the quantities of protein detected by ELISA assay in whole EVs were indicated for both the SerpinB3 over-expressing EVs and the control EVs.

Example 3

EV Quantification by Resistive Pulse Sensing

The quantification and characterization of EVs isolated from non-overexpressing and over-expressing SerpinB3 cells were performed using Resistive Pulse Sensing with qNANO instrumentation.

Resistive Pulse Sensing technology is designed to measure the number and size of nanoparticles in a liquid. The instrument is supplied with a membrane with a nanopore of known size inside an electrolytic fluid cell. The membrane impedance is sampled 50,000 times per second. The particles of the sample are guided through the nanopore by applying a combination of pressure and electric charge and each particle passing through the nanopore causes a change in impedance or "block" signal which is detected and measured by the application software.

The block size is directly proportional to the volume of each particle. The duration of the block changes with the speed of the particle and can be used to calculate the surface charge of each particle. The block frequency is used to determine the concentration of particles.

The magnitude, duration and frequency values are converted into respective particle properties by calibration with particles of known size, concentration and surface charge.

Figure 2A:
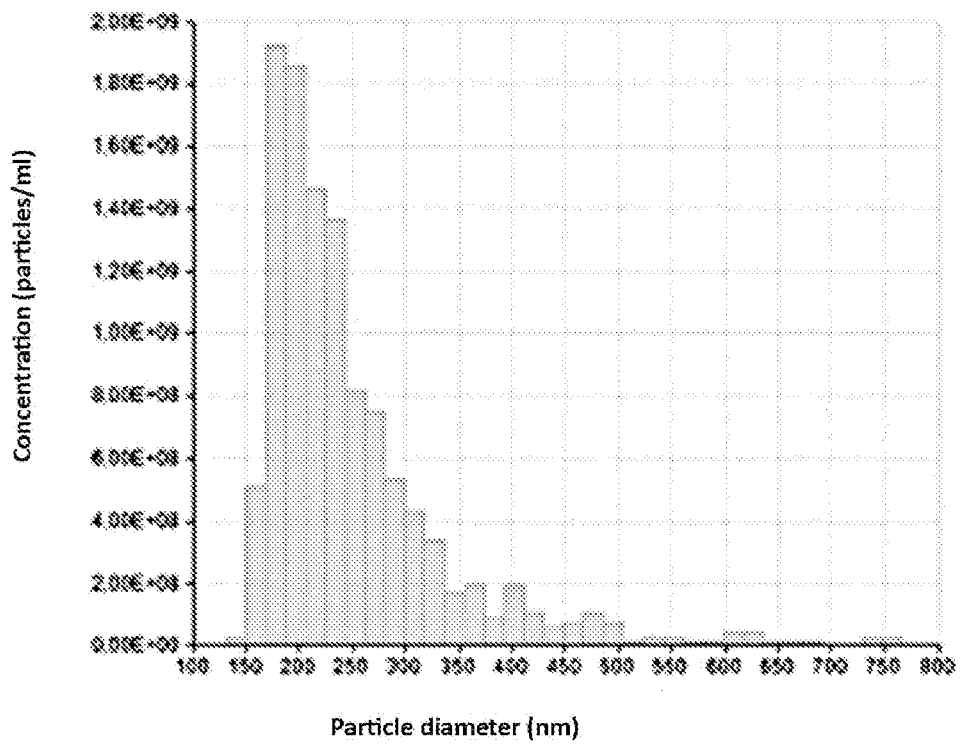
FIG. 2A shows data collected by Resistive Pulse Sensing (RPS) analysis with qNANO instrumentation in SerpinB3 over-expressing cells and FIG. 2B shows data collected by RPS in control cells.
Figure 2B:
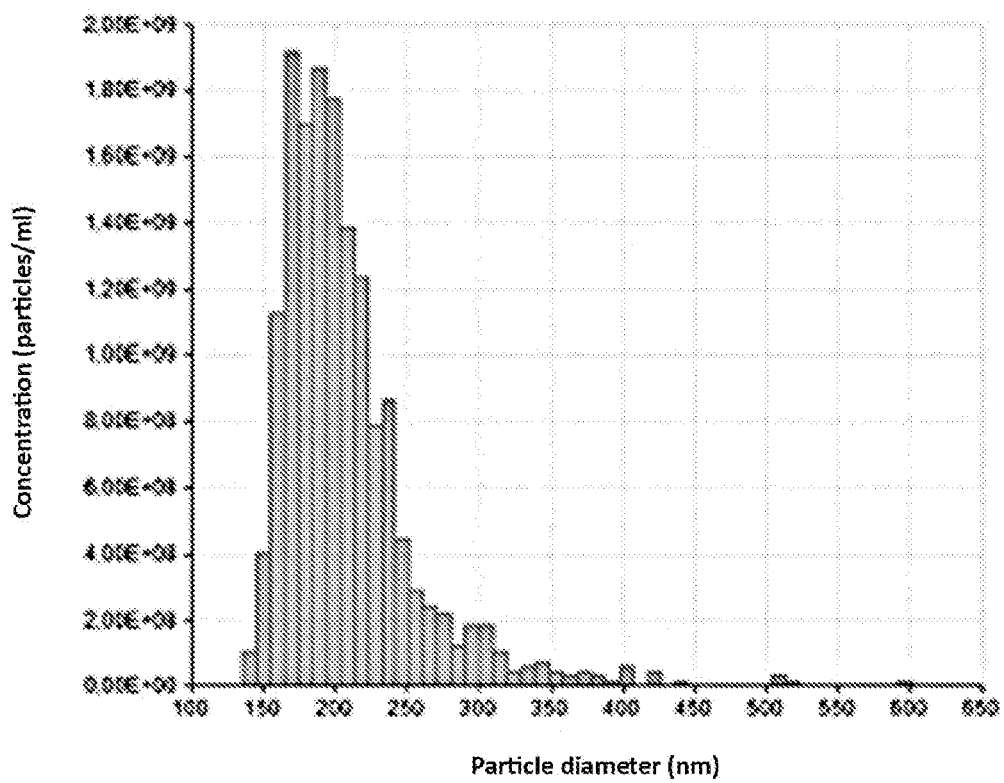

It has been possible to verify that the SERPINB3 over-expressing cells secrete a greater quantity of EV, and in particular that the SERPINB3 over-expressing cells release 32% more EV than non-overexpressing cells, as is evident from the graph shown in FIG. 2C, and from the results of the two cell lines (FIGS. 2A and 2B). It has also been possible to verify that the EVs released by these cells also have on average a larger size, as reported in Table 2.

TABLE 2

| EV size | SERPINB3 | CTRL |
| --- | --- | --- |
| Average diameter (nm) | 252 ± 94.3 | 209 ± 49.8 |
| Maximum diameter (nm) | 756 | 592 |
| Minimum diameter (nm) | 145 | 138 |

Example 4

Protection from Oxidative Damage by EV/SB3

As shown in FIG. 3, a cell mortality assay was performed by MTT assay, to verify the protection from oxidative damage by micro-vesicles that over-express SerpinB3 (EV/SB3). HepG2 cells at 90% of semiconfluence were treated with $H_2O_2$ 250 µMol and in parallel with control medium in the presence or absence of different EV preparations.

The following was tested:
- EVs deriving from HepG2 cells engineered to over-express SERPINB3=EV/SB3,
- EVs deriving from HepG2 cells transfected with the empty plasmid only=EV CTR,
- SerpinB3 recombinant protein at the same concentration present in the preparations of EV/SB3=rSB3; and
- EVs deriving from MSC=MSC EV.

All the EV preparations have been previously tested for SerpinB3 by ELISA and only the EV/SB3 preparation has tested positive, while the EV CTR and MSC EV preparations have not documented any detectable levels of SerpinB3. The results demonstrate for the first time how EVs deriving from HepG2 cells engineered to over-express SERPINB3 (EV SB3) promote a greater protection from oxidative damage induced by hydrogen peroxide, significantly higher than the control EVs (EV CTR) and the SERPINB3 recombinant protein (rSB3), used at the same concentrations present in SerpinB3 over-expressing EVs, but above all it is shown that EV SB3 bring about a greater protection from oxidative damage with respect to EVs produced by mesenchymal cells (MSC EV) which are not endowed with protective activity under these experimental conditions. The MSC EVs, which are known in the literature to be effective in promoting cellular protection, under the same experimental conditions, at these concentrations, are not able to protect cells treated with $H_2O_2$.

It can be concluded that only EV SB3 show a surprising effect in protecting cells from oxidative damage.

From the detailed description and from the Examples reported above, the advantages achieved by the EVs of the present invention are evident. In particular, these EVs turned out to be surprisingly and advantageously suitable for use as a medicament and in particular in the treatment of ischemic cell injury and cell injury due to oxidative stress. At the same time, the EVs of the present invention, being fast and extremely easy to prepare, can be conveniently made in conveniently equipped laboratories.

BIBLIOGRAPHICAL REFERENCES

1. Ciscato F, Sciacovelli M, Villano G, Turato C, Bernardi P, Rasola A, Pontisso P (2014). SerpinB3 protects from oidative damage by chemotherapeutics through inhibition of mithocondrial respratory complex I. Oncotarget 5:2418-2427.
2. Villano G, Turato C, Quarta S, Ruvoletto M, Ciscato F, Paternostro C, Parola M, Semeraro R, Alvaro D, Bernardi P, Gatta A, Pontisso P (2014). Hepatic progenitor cells over-express SerpinB3. BMC Cell Biol 15:5.
3. Cannito S, Turato C, Paternostro C, Biasiolo A, Colombatto S, Cambieri I, Quarta S, Novo E, Morello E, Villano G, Fasolato S, Musso T, David E, Tusa I, Rovida E, Autelli R, Smedile A, Cillo U, Pontisso P, Parola M (2015). Hypoxya up-regulates SerpinB3 through HIF-2a in human liver cancer cells. Oncotarget 6:2206-2221.
4. Turato C, Kent P, Sebastiani G, Cannito S, Morello E, Terrin L, Biasiolo A, Simonato D, Parola M, Pantopoulos K, Pontisso P (2018). SerpinB3 is over-expressed in the liver in presence of iron overload. J Invest Med 66:32-38.
5. Quarta S, Vidalino L, Turato C, Ruvoletto M, Calabrese F, Valente M, Cannito S, Fassina G, Parola M, Gatta A, Pontisso P (2010). SerpinB3 induces epithelial-mesenchymal transition. J Pathol 221:343-356.
6. Turato C, Cannito S, Simonato D, Villano G, Morello E, Terrin L, Quarta S, Biasiolo A, Ruvoletto M, Martini A, Fasolato S, Zanus G, Cillo U, Gatta A, Parola M, Pontisso P (2015) SerpinB3 and Yap interplay increases Myc oncogenic activity. Sci Rep 5:17701.
7. Kourembanas S (2015). Exosomes: Vehicles of Intercellular Signaling, Biomarkers, and Vectors of Cell Therapy. Annu Rev Physiol 77: 13-27.
8. Viaud S, C Théry, S Ploix, T Tursz, V Lapierre, O Lantz, L Zitvogel and N Chaput (2010). Dendritic cell-derived exosomes for cancer immunotherapy: what's next? Cancer Res 70: 1281-1285.
9. Muraca M, Piccoli M, Franzin C, Tolomeo AM, Jurga M, Pozzobon M and Perilongo G. Diverging Concepts and Novel Perspectives in Regenerative Medicine. Int. J. Mol. Sci. 2017, 18(5), 1021a; doi:10.3390/ijms18051021

The invention claimed is:

1. A method of using extracellular vesicles isolated from a cell line over-expressing SerpinB3 in subjects in need thereof, comprising:
   administering to said subjects an effective amount of said extracellular vesicles,
   wherein said vesicles are isolated from genetically modified cells over-expressing SerpinB3, and
   wherein a concentration of said SerpinB3 in said extracellular vesicles is increased relative to extracellular vesicles isolated from a cell line that does not overexpress SerpinB3.

2. The method according to claim 1, wherein said vesicles are used in the treatment of pathologies characterized by ischemic cell injury, wherein said pathologies are selected from the group consisting of myocardial, cerebral, intestinal or renal infarction, and acute limb ischemia.

3. The method according to claim 1, wherein said vesicles are used in the treatment of pathologies characterized by tissue damage due to oxidative stress, wherein said pathologies are selected from the group consisting of hypoxia of the donor organ in the context of heart, kidney, liver, lung, pancreas and intestine transplantation.

4. The method according to claim 1, wherein said vesicles are used in the treatment of pathologies characterized by acute inflammation.

5. The method according to claim 1, wherein said vesicles are isolated from genetically modified mesenchymal stromal cells over-expressing SerpinB3.

6. A pharmaceutical composition comprising extracellular vesicles isolated from genetically modified cells over-expressing SerpinB3 and a pharmaceutically acceptable vehicle,
wherein a concentration of said SerpinB3 in said extracellular vesicles is increased relative to extracellular vesicles isolated from a cell line that does not overexpress SerpinB3.

7. The pharmaceutical composition according to claim 6, wherein said vesicles are used in the treatment of the pathologies characterized by ischemic cell injury, wherein said pathologies are selected from the group consisting of myocardial, cerebral, intestinal or renal infarction, and acute limb ischemia.

8. The pharmaceutical composition according to claim 6, wherein said vesicles are used in the treatment of the pathologies characterized by cell injury due to oxidative stress, wherein said pathologies are selected from the group consisting of hypoxia of the donor organ in the context of heart, kidney, liver, lung, pancreas and intestine transplantation.

9. The pharmaceutical composition according to claim 6, wherein said vesicles are used in the treatment of the pathologies characterized by cell injury due to acute inflammation.

10. The pharmaceutical composition according to claim 9, wherein the cell injury is an injury to cardiac cells, brain cells, intestinal cells, renal cells or limb cells.

11. The pharmaceutical composition according to claim 9, wherein the cell injury is an injury due to toxic substances, wherein said toxic substances are selected from the group consisting of alcohol and cigarette smoke.

12. The pharmaceutical composition according to claim 6, wherein said composition is in a solid or in a liquid form, and wherein said composition is for enteral or parenteral administration, for intravenous, intraperitoneal, oral, sublingual, aerosol, inhalation, spray, rectal, intraocular, topical or transdermal administration.

13. A method of using extracellular vesicles isolated from genetically modified cells over-expressing SerpinB3 for the preservation of transplant organs,
wherein a concentration of said SerpinB3 in said extracellular vesicles is increased relative to extracellular vesicles isolated from a cell line that does not overexpress SerpinB3.

14. The method of use according to claim 13, wherein said transplant organs are selected from the group consisting of heart, lung, liver, bladder, pancreas and intestine.

* * * * *